(12) United States Patent
Ramakrishnan et al.

(10) Patent No.: US 7,134,500 B2
(45) Date of Patent: Nov. 14, 2006

(54) FORMATION FLUID CHARACTERIZATION USING FLOWLINE VISCOSITY AND DENSITY DATA AN OIL-BASED MUD ENVIRONMENT

(75) Inventors: Terizhandur S. Ramakrishnan, Bethel, CT (US); Soraya Sofia Betancourt, Ridgefield, CT (US)

(73) Assignee: Schlumberger Technology Corporation, Ridgefield, CT (US)

( * ) Notice: Subject to any disclaimer, the term of this patent is extended or adjusted under 35 U.S.C. 154(b) by 198 days.

(21) Appl. No.: 10/741,078

(22) Filed: Dec. 19, 2003

(65) Prior Publication Data

US 2005/0133261 A1    Jun. 23, 2005

(51) Int. Cl.
*E21B 43/00* (2006.01)
(52) U.S. Cl. ......................................... 166/369; 175/40
(58) Field of Classification Search .................... None
See application file for complete search history.

(56) References Cited

U.S. PATENT DOCUMENTS

| 4,860,581 | A  |   | 8/1989 | Zimmerman et al. ......... 73/155 |
| 6,108,608 | A  | * | 8/2000 | Watts, III ..................... 702/30 |
| 6,234,030 | B1 | * | 5/2001 | Butler ..................... 73/861.04 |
| 6,343,507 | B1 | * | 2/2002 | Felling et al. ........... 73/152.19 |
| 6,799,117 | B1 | * | 9/2004 | Proett et al. ................... 702/12 |

OTHER PUBLICATIONS

Andrews, R.J. et al. *Quantifying Contamination Using Color of Crude and Condensate*. Oilfield Review, 13 (2001) pp. 24-43.

Ayan et al. *Characterizing Permeability with Formation Testers*. Oilfield Review 13(2001) pp. 2-23.
Batchelor, G. K. *An Introduction to Fluid Dynamics*. Cambridge University Press, New York (1967) pp. 246-253.
Bird, R.B. et al. *Transport Phenomena* John Wiley and Sons, New York (2002) pp. 533-535.
Chilingarian, G. et al. *Drilling and Drilling Fluids*. Elsevier, New York (1983) pp. 365-366.
Goldstein, R.J. *Fluid Mechanics Measurements*. Hemisphere Publishing. New York (1983) pp. 538-549.
Imano, K. et al. *Viscosity of Liquid Using Piezoceramic Disk Transducer with a Radial Expansion Mode*. IEICE Trans. Fund. E83-A(1), (2000) pp. 162-163.
Kleinberg, R.L. et al. *NMR Properties of Reservoir Fluids. The Log Analyst*. 37(1996) pp. 20-32.
Perry, R.H. et al. *Chemical Engineers' Handbook*. McGraw-Hill, New York. (1973) p. 247.
Press W.H. et al. *Numerical Recipes in Fortran*. Cambridge University Press. New York (1992) pp. 653-655 and pp. 660-662.

(Continued)

*Primary Examiner*—Frank Tsay
(74) *Attorney, Agent, or Firm*—David P. Gordon; Jody Lynn DeStefanis; Dale Gaudier

(57) ABSTRACT

A method for characterizing formation fluid using flowline viscosity and density data in an oil-based mud environment includes: making an initial estimate of the density and viscosity of the individual components of the sampled fluid; measuring the volume fractions, density, and viscosity of the total mixture of formation fluid; computing the density and viscosity of the total mixture using the estimate and the measured volume fractions; comparing the computed values with the measured values; and updating the estimate based on the comparison until convergence. The process is repeated as additional data are acquired until the converged computed values differ only by an acceptable amount.

27 Claims, 1 Drawing Sheet

OTHER PUBLICATIONS

Reid, R.C. et al. *The Properties of Gases and Liquids*. McGraw-Hill, New York (1987) pp. 472-483.

Van Geet, A.L. et al. *Diffusion in Liquid Hydrocarbon Mixtures. J. Phys. Chem* 68(2) (1964) pp. 238-246.

* cited by examiner

FORMATION FLUID CHARACTERIZATION USING FLOWLINE VISCOSITY AND DENSITY DATA AN OIL-BASED MUD ENVIRONMENT

BACKGROUND OF THE INVENTION

1. Field of the Invention

This invention relates broadly to oil exploration and production. More particularly, this invention relates to methods for determining the viscosity and density of formation fluids.

2. State of the Art

Various methods and tools are used to describe reservoir fluid and formation properties in an oil well. Some of these methods and tools aim to determine the relative volume of oil, water, and gas, for example. Other methods and tools aim to qualitatively describe the reservoir oil. This can be done by sampling the oil and by determining the density and viscosity of the sampled oil. However, when the sampled fluid is contaminated with mud-filtrate, making a direct measurement of reservoir oil density and/or viscosity is difficult.

Using the Schlumberger Modular Formation Dynamics Tester (MDT), fluid samples can be taken from the formation wall. Modules in the MDT test the samples in a variety of ways and with appropriate sensors could provide density and viscosity measurements for the mixture sampled. If the mixture were pure formation fluid, characterization of the oil in the reservoir could be accurately determined. However, the fluid is nearly always contaminated with at least some drilling mud. This prevents an absolutely accurate characterization of the oil in the reservoir.

During the drilling process, mud is pumped into the wellbore surrounding the drilling tool. The mud serves several purposes. It acts as a buoyant medium, cuttings transporter, lubricant, coolant, as well as a medium through which downhole telemetry may be achieved. The mud is usually kept overbalanced, i.e. at a higher pressure than the pressure of the formation fluids. This leads to "invasion" of the mud into the formation and the buildup of mudcake on the borehole wall. This is the environment in which samples are taken with a tool such as the MDT. Although the MDT filters out the solids from the samples, mud filtrate is always present in the samples.

When the mud filtrate is immiscible with the formation fluids, it is possible to separate it from the formation fluids by centrifuge or by settling due to gravity. However, when a well is drilled with oil-based-mud (OBM) the filtrate may miscibly mix with the formation fluid. When samples are taken, the first samples are nearly all OBM and if one waits long enough the last samples are nearly all formation fluid. However, it is unlikely that even the last sample will be pure enough to provide highly accurate measurements of viscosity and density of the formation fluids.

SUMMARY OF THE INVENTION

It is therefore an object of the invention to provide methods for determining the viscosity and density of formation fluids in a well which was drilled with OBM.

It is another object of the invention to provide methods for determining the viscosity and density of formation fluids based on measurements of samples containing formation fluids mixed with OBM.

In accord with these objects, which will be discussed in detail below, the methods of the present invention utilize a mixing model which is capable of accurately predicting viscosity and density of a mixture of formation fluids and OBM based on viscosity and density of the individual components and the volume fractions of the components. The methods further include starting with an initial estimate of the properties of the individual components of the mixture, measuring the volume fractions of the mixture, applying the mixing model, measuring the viscosity and density of the mixture and comparing the measurement to the mixing model results. The process is repeated iteratively with updated estimates until error in the determination of density and viscosity of the components is minimized (i.e., converges), thereby providing determinations of component properties. If desired, new data are acquired, and additional determinations of component properties may be obtained. The determinations of component properties may then be compared to see if they are within a desired tolerance (i.e., to see whether they converge). When it is apparent that the addition of new data makes no difference to the estimated component properties, the process may be concluded.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
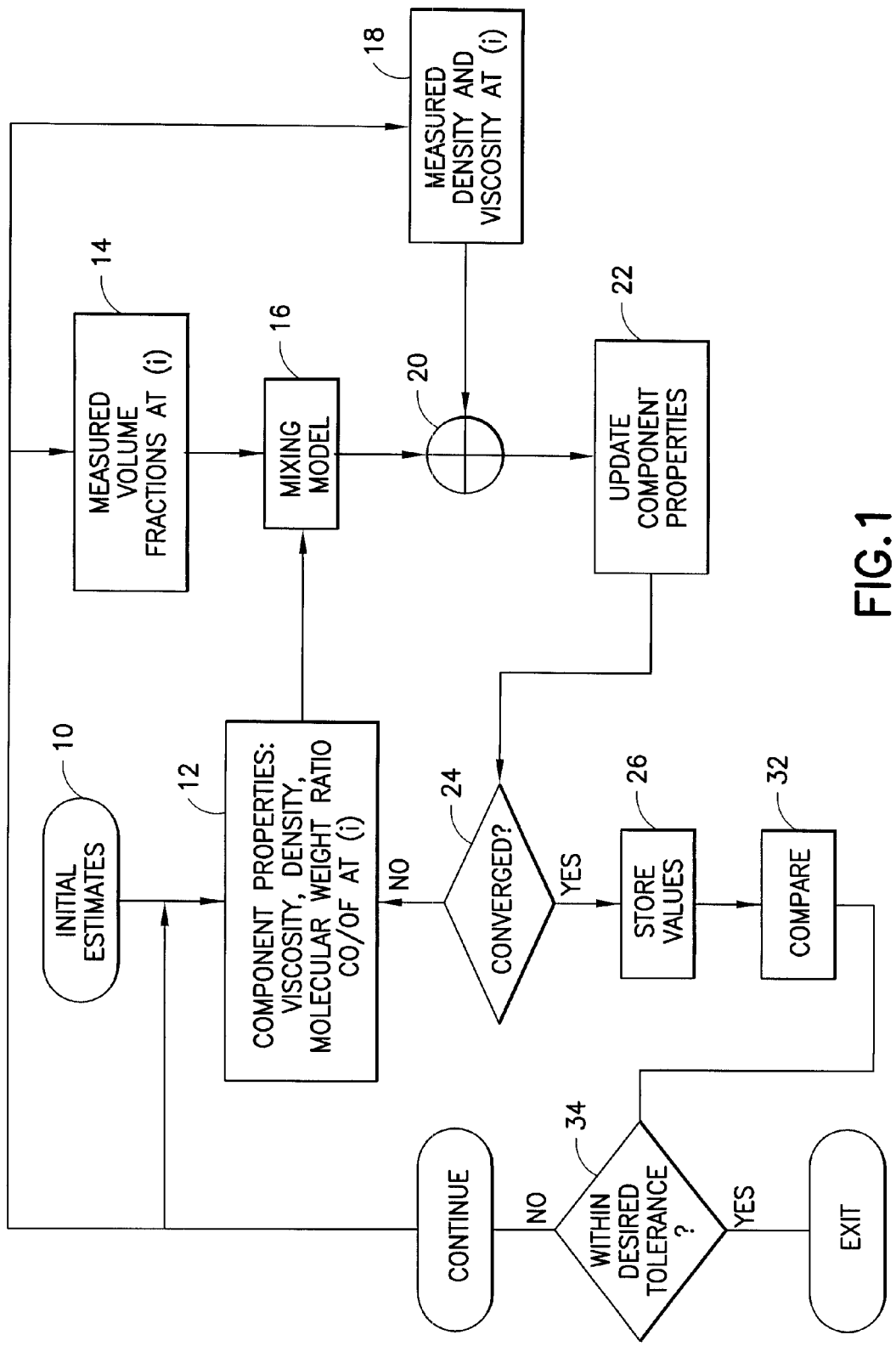
FIG. 1 is a schematic flow chart illustrating the iterative methods of the invention.

Before turning to the FIGURE, the mixing models according to the invention will be described. In the equations described below, the following notation is used:

M is molecular weight,
x is mole fraction,
w is weight fraction,
z is volume fraction,
$\rho$ is density, and
$\mu$ is viscosity.

The following subscripts are used in conjunction with the variables listed above:

co is crude oil,
of is the oil part of OBM filtrate,
o is the crude oil+oil filtrate mixture,
t is the total mixture containing water in mud-filtrate emulsion and crude oil resulting from calculations, and
tm is the total mixture containing water in mud-filtrate emulsion and crude oil resulting from measurement.

When three components, namely crude oil, oil filtrate and water are involved, but the properties are normalized with respect to the oil external phase, i.e. excluding water, a ^ is placed over the fraction variable.

An OBM may include a water phase in the form of a water-in-oil (W/O) emulsion. Usually, the amount of water is small, about 10% or less, but sufficient to introduce a complication in the mixing models. When another hydrocarbon comes in contact with this emulsion, the hydrocarbon portions will mix, and a diluted W/O emulsion is formed. Additionally, the water in the emulsion may be trapped in the mudcake, or have low mobility in the formation to be effectively trapped. It is often found that the sampled fluid does not have the water fraction expected based on the water fraction of the mud. For handling cases ranging from complete water trapping to zero water trapping (all of the original water flows back), the invention provides several options. These include using the water fraction as measured, forcing the water fraction to be zero, or accepting the original water fraction of the OBM.

For the first part of the mixing model, it is assumed that the OBM does not contain water and the mud and the reservoir fluids are completely miscible. When the crude oil and the OBM filtrate mix, mass is conserved. For purposes of the mixing model, it is also assumed that volume is conserved. This assumption is equivalent to zero volume of mixing. The density of the crude oil and oil filtrate mixture can be determined from Equation (1).

$$\rho = \sum_{i=co, of} \rho_i z_i \quad (1)$$

The viscosity of the crude oil and oil filtrate mixture can be determined from the power rule which is shown as Equation 2.

$$\mu_o^{1/3} = x_{of} \mu_{of}^{1/3} + x_{co} \mu_{co}^{1/3} \quad (2)$$

It should be noted that Equation (2) can be found in R. H. Perry and C. H. Chilton, "Chemical Engineer's Handbook", McGraw-Hill, New York, 1973.

The invention assumes that a downhole tool is providing volume fractions of the sampled mixture over time. Thus, the weight fraction of crude oil can be determined with Equation (3).

$$w_{co} = \frac{z_{co} \rho_{co}}{z_{co} \rho_{co} + z_{of} \rho_{of}} \quad (3)$$

Those skilled in the art will appreciate that the weight fraction of the oil part of the filtrate can be determined with Equation (3a).

$$w_{of} = 1 - w_{co} \quad (3a)$$

Given the weight fractions and the densities, the volume fractions of the crude oil and the oil part of the filtrate can be determined with Equations (4) and (4a) respectively.

$$z_{co} = \frac{\frac{w_{co}}{\rho_{co}}}{\frac{w_{co}}{\rho_{co}} + \frac{w_{of}}{\rho_{of}}} \quad (4)$$

$$z_{of} = 1 - z_{co} \quad (4a)$$

It should be recalled that the ultimate goal of the methods of the invention is to determine density and viscosity of each component of the sampled fluid over time given the volume fractions, the mixture density, and viscosity supplied over time by the downhole tool and initial estimates. The density is easily computed using Equation (1). However, in order to determine viscosity using Equation (2), the mole fractions of the crude oil and the oil part of the filtrate must be known. The mole fractions can be determined with Equations (5) and (5a).

$$x_{co} = \frac{\frac{w_{co}}{M_{co}}}{\frac{w_{co}}{M_{co}} + \frac{w_{of}}{M_{of}}} = \frac{w_{co} R_M}{w_{co} R_M + w_{of}} \quad (5)$$

$$R_M = \frac{M_{of}}{M_{co}} \quad (5a)$$

According to the presently preferred embodiment, Equations (6), (6a), and (6b) are used to compute the mole fractions of the components in order to solve Equation (2).

$$x_{co} = \frac{\frac{z_{co} \rho_{co}}{M_{co}}}{\frac{z_{co} \rho_{co}}{M_{co}} + \frac{z_{of} \rho_{of}}{M_{of}}}$$

$$= \frac{z_{co} \rho_{co} R_M}{z_{co} \rho_{co} R_M + z_{of} \rho_{of}}$$

$$= \frac{\frac{z_{co}}{\alpha_{co}}}{\frac{z_{co}}{\alpha_{co}} + \frac{z_{of}}{\alpha_{of}}} = \frac{z_{co} R_\alpha}{z_{co} R_\alpha + z_{of}} \quad (6)$$

$$\frac{M_i}{\rho_i} = \alpha_i \quad (6a)$$

$$R_\alpha = \frac{\alpha_{of}}{\alpha_{co}} \quad (6b)$$

Given the mole fractions and molecular weights, the weight fractions can be computed using Equation (7)

$$w_{co} = \frac{x_{co} M_{co}}{x_{co} M_{co} + x_{of} M_{of}} \quad (7)$$

and the volume fractions can be computed using Equation (8).

$$z_{co} = \frac{\frac{x_{co} M_{co}}{\rho_{co}}}{\frac{x_{co} M_{co}}{\rho_{co}} + \frac{x_{of} M_{of}}{\rho_{of}}} \quad (8)$$

After the density and viscosity of the mixture are calculated using Equations (1) and (2), the values are compared to the measured density and viscosity of the mixture as obtained from the downhole tool as described in more detail below with reference to FIG. 1 and Equation (17). Before continuing with the methods of the invention, the calculations for OBM containing water are considered. Many oil based muds contain water in oil emulsions. Water is added to the mud along with suitable dispersive agents to enhance the plastering and rheological properties of the mud. The dispersed water droplets are almost uniform in size. A readily mixed OBM containing water may contain 2–7% water. See, e.g., G. Chilingarian and P. Vorabutr, "Drilling and Drilling Fluids," Elsevier, New York, 1983. Diesel oil is widely used as the external oil phase.

An emulsion of water in oil has a higher viscosity than the viscosity of the continuous phase (the oil), and the viscosity increases as water content increases. For dilute emulsions, an effective viscosity of the mixture may be obtained using Equation (9) as taught by G. K. Batchelor, "An Introduction to Fluid Dynamics," Cambridge University Press, New York, 1967.

$$\frac{\mu_1}{\mu_o} = 1 + z_w \left( \frac{\mu_o + \frac{5}{2}\mu_w}{\mu_o + \mu_w} \right) \quad (9)$$

It is assumed that the filtrate oil and the crude oil miscibly mix to create an oil phase with a viscosity $\mu_o$ as determined by Equation (10).

$$\mu_o^{1/3} = \mu_{co}^{1/3}\left[\frac{\hat{z}_{co}\rho_{co}R_M}{\hat{z}_{co}\rho_{co}R_M + \hat{z}_{of}\rho_{of}M_{of}}\right] + \mu_{of}^{1/3}\left[\frac{\hat{z}_{of}\rho_{of}}{\hat{z}_{co}\rho_{co}R_M + \hat{z}_{of}\rho_{of}}\right] \quad (10)$$

It should be noted that Equation (10) is expressed in normalized volume fractions with respect to the oil phase. How these normalized volume fractions relate to the actual volume fractions depends on assumptions which are described below with reference to Equations (12) through (16).

It will be appreciated that Equations (10) and (9) are used to determine viscosity of the total mixture.

Equation (11) is used to determine density of the total mixture.

$$\rho_t = \sum_{i=co,of,w} \rho_i z_i \quad (11)$$

Three different assumptions are considered with regard to the volume fraction of water in the sampled fluid. In the first case it is assumed that the volume fraction $z_w$ is directly measured and accepted as the true value. In this case, the normalized volume fractions of crude oil and oil filtrate are calculated as shown in Equations (12) and (13).

$$\hat{z}_{co} = \frac{z_{co}}{z_{co} + z_{of}} \quad (12)$$

$$\hat{z}_{of} = \frac{z_{of}}{z_{co} + z_{of}} \quad (13)$$

Then the density and viscosity of the total mixture is determined by applying Equations (10), (9), and (11).

In the second case, it is assumed that the volume fraction $z_w$ is difficult to measure without error and the water droplets are either trapped by the mudcake or inside the rock formation during sampling. In this case, $z_w$ is taken to be zero. Thus, the measured volume fractions of the oil phase add to unity (i.e., $z_{co}+z_{of}=1$) and are the same as the normalized volume fractions. Equation (10) is sufficient to determine total viscosity because $\mu_t=\mu_o$. Further $\rho_t=\rho_o$.

In the third case, it is assumed that the volume fraction $z_w$ is the same as the original constitution of the OBM. This may be the case when the volume fraction $z_w$ cannot be correctly measured, but there is reason to believe that water trapping does not occur. In this case it is also assumed that the measured volume fractions of crude oil and oil filtrate are correct in terms of their ratio, that they are the same as the normalized volume fractions and add up to unity. The volume fraction of water is assigned so that the volume fractions of water and oil filtrate are the same as the constitution of the OBM. Equations (14) and (15) illustrate how the volume fraction of water $z_w$ can be determined from the volume fraction of the water in the OBM as originally constituted $z_w^0$ and the normalized volume fraction of oil filtrate $\hat{z}_{of}$.

$$z_w^0 = \frac{z_w}{(1-z_w)\hat{z}_{of} + z_w} \quad (14)$$

$$z_w = \frac{z_w^0 \hat{z}_{of}}{1 + z_w^0 \hat{z}_{of} - z_w^0} \quad (15)$$

Given these assumptions and the computed volume fraction of water, Equations (10) and (9) can be used to determine viscosity of the total mixture and Equation (16) can be used to determine the density of the total mixture.

$$\rho_t = \rho_{co}\hat{z}_{co}(1-z_w) + \rho_{of}\hat{z}_{of}(1-z_w) + \rho_w z_w \quad (16)$$

In performing the computational procedure of the invention, it is assumed that downhole measurements provide a one-dimensional (column) vector of values for density, viscosity and volume fractions of water (if present) and oil filtrate for the mixture. Each measurement time point corresponds to a row number for these vectors, which forms a matrix. A row of the matrix forms a time point of density, viscosity, and volume fractions. Herein below, the row number of this matrix is denoted by the superscript (i).

The measured volume fraction for oil filtrate is accepted as correct. The measured volume fraction for water is either (1) accepted as correct, (2) assumed to be incorrect and is set to zero, or (3) assumed to be incorrect and set to the volume fraction of water in the OBM as described above. Depending on case (1), (2), or (3), the volume fractions are "conditioned" as follows.

In case (1), the volume fraction for crude oil is calculated by subtracting the volume fractions for oil filtrate and water from 1. If the volume fraction for water is measured to be zero, only the volume fraction for oil filtrate is used in the computations. For case (2), where the measured volume fraction of water is not zero but is set to zero, the measured volume fraction for oil filtrate is renormalized using Equation (13). For case (3), the volume fraction for water is calculated from the original OBM volume fraction using Equation (15).

A row vector for each time point following conditioning are the numbers $\rho_{tm}^{(i)}$, $\mu_{tm}^{(i)}$, $z_w^{(i)}$, $z_{of}^{(i)}$, $z_{co}^{(i)}$, $\hat{z}_{of}^{(i)}$, $\hat{z}_{co}^{(i)}$. Using the volume fractions from this vector as given and the initial estimates of the densities and viscosities of oil filtrate, crude oil, and water (known independently), the viscosity and density of the total mixture are computed using Equations (9) and (16). The computed viscosity and density ($\mu_t$, $\rho_t$) of the total mixture are compared to the measured viscosity and density of the total mixture ($\mu_{tm}$, $\rho_{tm}$) and the error is calculated using Equation (17)

$$E = \sum_{i=1}^{N} \frac{1}{\sigma_\rho^{(i)2}} (\rho_t^{(i)} - \rho_{tm}^{(i)})^2 + \frac{1}{\sigma_\mu^{(i)2}} (\mu_t^{(i)} - \mu_{tm}^{(i)})^2 \quad (17)$$

where N is the number of time points, and where $\sigma_\rho^2$ and $\sigma_\mu^2$ are the variances in the measurements of $\rho$ and $\mu$. In the absence of any additional information they may be chosen proportional to $\rho_{tm}^2$ and $\mu_{tm}^2$ respectively. The difference between the output of the mixing model and the measured values (i.e. the error E) is minimized using a gradient method with a Levenburg-Marquardt step controller. See, for instance, W. H. Press, S. A. Teukolsky, W. T T. Vetterling, and B. P. Flannery. *Numerical recipes in Fortran*. Cambridge University Press, New York, 1992.

Given all of the above, the method of the invention can be described in flow-chart form. Referring now to FIG. 1, starting at 10 initial estimates (e.g., educated guesses) are made regarding the viscosity and density of the crude oil and oil filtrate as well as their molecular weight ratio at 12 of the downhole mixture of formation fluid and OBM. The initial estimates are made on the basis of knowledge from other nearby wells and the known constitution of the OBM. The measured volume fractions for this iteration are acquired at 14 using the MDT. See, for instance, R. J. Andrews, G. Beck, K. Castelijns, J. Chen, M. E. Cribbs, F. H. Fadness, J. Invin-Fortescue, S. Williams, M. Hashem, A. Jamaluddin, A. Kurkjian, B. Sass, O. C. Mullins, E. Rylander, and A. Van Dusen. Quantifying contamination using color of crude and condensate. *Oilfield Review*, 13, 24–43, 2001. Using the initial estimates and the measured (and conditioned if necessary) volume fractions, the mixing model (Equations (9) and (16)) is applied at 16. As explained above, the conditioning of the measured fractions will depend on assumptions made regarding the expected water fraction.

The measured density and viscosity of the mixture for this iteration may be acquired at 18 using sensors within the fluid sampling device such as the MDT (see for instance: R. J. Goldstein. *Fluid mechanics measurements*. Hemisphere publishing, New York, 1983; K. Imano, R. Shimazaki, and S. Momozawa. Viscosity of liquid using piezoceramic disk transducer with a radial expansion mode. *IEICE Trans. Fund.*, E83-A(1), 162–163, 2000; and R. L. Kleinberg and H. J. Vinegar. NMR properties of reservoir fluids. *The Log Analyst*, 37, 20–32, 1996) and are compared to the mixing model output at 20. The difference is minimized and the initial estimates regarding the component properties are updated at 22 using a least squares algorithm as described above. The iterative trend is analyzed for convergence to error minimization at 24 using Equation (17). If there is no convergence, the component properties are updated at 12 and applied to the mixing model at 16. If the difference is minimized, the updated component properties are accepted for the provided data set, and the error minimization process ends at 26 for that data set by storing values for the component properties.

According to the preferred embodiment of the invention, if desired, the stored values for different times (i) may be compared at 32 to see whether they converge on determinations of component properties. For example, the determinations of component properties for, e.g., i=1, 2, ..., N, and i=1, 2, ... 2N may be compared at 32 to see if they are within a desired tolerance (i.e., to see whether they converge to particular values). If at 34 it is determined that they are not within a desired tolerance, new data may be acquired (at times i=2N+1, 2N+2, ... ), and additional determinations of component properties may be obtained utilizing error minimization as described above with reference to steps 10–26. When it is apparent at 34 that the addition of new data makes no difference to the estimated component properties (i.e., they have converged), the process may be concluded. More particularly, at the given time $t_{(N)}$ consisting of measurements 1, 2, ... i, ... N the stored component properties will be the values for the component properties determined at that point $t_{(N)}$. If an additional measurement at time $t_{(N+1)}$ is made, the component properties of the previous time $t_{(N)}$ becomes the initial estimate for the least squares algorithm for points 1, 2, ..., i, ... N, N+1 and values for a new converged component property set may be determined. If the difference between the component properties obtained at time $t_N$ and a later time, e.g., $t_{2N}$ are within a tolerance of the form:

$$\left| \frac{\rho_{of,N} - \rho_{of,2N}}{\rho_{of,2N}} \right| \leq E_{\rho,of} \quad (18)$$

$$\left| \frac{\rho_{co,N} - \rho_{co,2N}}{\rho_{co,2N}} \right| \leq E_{\rho,co} \quad (19)$$

$$\left| \frac{\mu_{of,N} - \mu_{of,2N}}{\mu_{of,2N}} \right| \leq E_{\mu,of} \quad (20)$$

$$\left| \frac{\mu_{co,N} - \mu_{co,2N}}{\mu_{co,2N}} \right| \leq E_{\mu,co} \quad (21)$$

then the final determination for the component properties may be considered acceptable and the sampling process may be stopped if desired. If desired, one or more additional tolerances (e.g., the molecular weight ratio) may be utilized.

There have been described and illustrated herein a method for characterizing formation fluid using flowline viscosity and density data in an oil-based mud environment. While particular embodiments of the invention have been described, it is not intended that the invention be limited thereto, as it is intended that the invention be as broad in scope as the art will allow and that the specification be read likewise. Thus, while a determination of both density and viscosity are described, it will be appreciated that the methods of the invention may be utilized to obtain information regarding either density or viscosity. Also, while particular equations were utilized with respect to density and viscosity and while particular assumptions were made with respect to mixing, it will be appreciated that other equations and assumptions could be utilized. Similarly, while certain scenarios were described with reference to the volume fraction of water, it will be appreciated that other assumptions could be utilized. Further, while the invention was described with respect to a particular least squares algorithm for error minimization, it will be appreciated that other algorithms could be utilized. Likewise, while particular times (N and 2N) were provided as an example for comparing component property values for determining convergence over time, it will be appreciated that the convergence (tolerance) determination could be made after every sampling time (e.g., by comparing values at times N and N+1), or after every predetermined number of sampling periods, or otherwise as desired. It will therefore be appreciated by those skilled in the art that yet other modifications could be made to the provided invention without deviating from its spirit and scope as claimed.

What is claimed is:

1. A method for characterizing formation fluid using flowline viscosity and density data in an oil-based mud (OBM) environment, said method comprising:
   a) providing an initial estimate of at least one of the density and viscosity of the crude oil and oil filtrate components of the mixture of formation fluid and OBM;
   b) measuring the volume fractions, and at least one of the density and viscosity of the total mixture of formation fluid and OBM;
   c) computing at least one of the density and viscosity of the total mixture using the estimate of at least one of the density and viscosity and the measured volume fractions;
   d) comparing the at least one of the computed density and viscosity of the total mixture with the at least one of the measured density and viscosity of the total mixture; and
   e) charactexizing the formation fluid by updating the estimate of the at least one of the density and viscosity of the individual components of the formation fluid based on the comparison of the computed density and viscosity of the total mixture with the measured density and viscosity of the total mixture.

2. The method according to claim 1, wherein:
said step of measuring is performed with an optical fluid analyzer.

3. The method according to claim 1, further comprising:
   f) normalizing the volume fraction of crude oil and oil filtrate prior to computing density, wherein
said step of computing density is performed according to $$\rho_t = \rho_{co}\hat{z}_{co}(1-z_w) + \rho_{of}\hat{z}_{of}(1-z_w) + \rho_w z_w$$

where $\rho_t$ is density of the total mixture, $\rho_{co}$ is the density of crude oil, $\hat{z}_{co}$ is the normalized volume fraction of crude oil, $z_{co}$ is the volume fraction of water, $\rho_{of}$ is the density of oil filtrate, $\hat{z}_{of}$ is the normalized volume fraction of oil filtrate, and $\rho_w$ is the density of water.

4. The method according to claim 3, wherein:
the normalized volume fraction of crude oil $\hat{z}_{co}$ is computed according to $$\hat{z}_{co} = \frac{z_{co}}{z_{co} + z_{of}}$$

where $z_{co}$ is the volume fraction of crude oil, and $z_{of}$ is the volume fraction of oil filtrate.

5. The method according to claim 4, wherein:
the normalized volume fraction of oil filtrate $\hat{z}_{of}$ is computed according to.

$$\hat{z}_{of} = \frac{z_{of}}{z_{co} + z_{of}}.$$

6. The method according to claim 1, wherein:
said step of computing viscosity is performed according to $$\frac{\mu_t}{\mu_o} = 1 + z_w \left( \frac{\mu_o + \frac{5}{2}\mu_w}{\mu_o + \mu_w} \right)$$

where $\mu_t$ is the viscosity of the total mixture, $\mu_o$ is the viscosity of the crude oil and oil filtrate mixture, $z_w$ is the volume fraction of water, and $\mu_w$ is the viscosity of water.

7. The method according to claim 5, wherein:
the volume fraction of water is not measured but is computed according to $$z_w = \frac{z_w^0 \hat{z}_{of}}{1 + z_w^0 \hat{z}_{of} - z_w^0}$$

where $z_w^0$ is the volume fraction of the water in the OBM as originally constituted and $\hat{z}_{of}$ is the normalized volume fraction of oil filtrate.

8. The method according to claim 1, wherein:
the volume fraction of water is taken to be zero regardless of what is measured and $z_{co} + z_{of} = 1$ where $z_{co}$ is the volume fraction of crude oil and $z_{of}$ is the volume fraction of oil filtrate.

9. The method according to claim 1, further comprising:
iteratively repeating steps (b) through (e), wherein said estimate of said computing step is an updated estimated provided by said updating step.

10. The method according to claim 9, wherein:
said step of updating is performed with a least squares algorithm.

11. The method according to claim 10, wherein:
said step of comparing is performed according to $$E = \sum_{i=1}^{N} \frac{1}{\sigma_\rho^{(i)2}}(\rho_t^{(i)} - \rho_{tm}^{(i)})^2 + \frac{1}{\sigma_\mu^{(i)2}}(\mu_t^{(i)} - \mu_{tm}^{(i)})^2$$

where $\rho_t^{(i)}$ is the calculated density of the total mixture at iteration (i), $\rho_{tm}^{(i)}$ is the measured density of the total mixture at iteration (i), $\mu_t^{(i)}$ is the calculated viscosity of the total mixture at iteration (i), $\mu_{tm}^{(i)}$ is the measured viscosity of the total mixture at iteration (i), $\sigma_\rho^{(i)2}$ is the variance in $\rho_{tm}(i)$, $\sigma_\mu^{(i)2}$ is the variance in $\mu_{tm}(i)$, E is an error, and N is the total number of time points considered.

12. The method according to claim 11, wherein:
said least squares algorithm is an error minimization algorithm which is performed with (N) number of measured and calculated densities and viscosities of crude oil and oil filtrate in order to provide a calculation of at least one of said crude oil density and said crude oil viscosity.

13. The method according to claim 12, further comprising:
comparing determinations of said at least one of the density and viscosity of the total mixture made at different sampling times to make a final estimate of the component properties.

14. The method according to claim 13, wherein:
said comparing determinations comprises comparing determinations of both said density and viscosity to determine whether said comparisons are within a desired tolerance.

15. A method for characterizing hydrocarbon fluid in a reservoir, comprising:
   a) estimating the expected viscosity and density of the components of the hydrocarbon fluid;

b) calculating the density and viscosity of the hydrocarbon fluid based on the estimates of the viscosity and density of the components;

c) measuring the viscosity and density of the hydrocarbon fluid;

d) comparing the calculated density and viscosity of the hydrocarbon fluid with the measured density and viscosity; and e) characterizing the hydrocarbon fluid in the reservoir by updating the estimates of the viscosity and density of the components based on the comparison.

16. The method according to claim 15, further comprising:

f) drilling a wellbore into the reservoir formation prior to said step of measuring, wherein said step of estimating is performed with knowledge about the reservoir and the mud used during drilling.

17. The method according to claim 15, further comprising:

f) determining the volume fractions of the hydrocarbon fluid by measurement prior to said step of calculating.

18. The method according to claim 17, wherein:

said step of calculating the density and viscosity of the hydrocarbon fluid is based on the determination of volume fractions as well as on the estimates of the viscosity and density of the components.

19. The method according to claim 15, wherein:

said step of measuring includes sampling fluid with a flow-line device.

20. The method according to claim 15, wherein:

said step of comparing includes application of a least squares algorithm.

21. The method according to claim 15, wherein:

said step of computing density includes computing a normalized volume fraction of crude oil and a normalized volume fraction of oil filtrate.

22. The method according to claim 15, further comprising:

iteratively repeating steps (b) through (e), wherein said estimate of said calculating step is an updated estimated provided by said updating step.

23. The method according to claim 22, wherein:

said step of updating is performed with a least squares algorithm.

24. The method according to claim 23, wherein:

said step of comparing is performed according to $$E = \sum_{i=1}^{N} \frac{1}{\sigma_\rho^{(i)2}} (\rho_t^{(i)} - \rho_{tm}^{(i)})^2 + \frac{1}{\sigma_\mu^{(i)2}} (\mu_t^{(i)} - \mu_{tm}^{(i)})^2$$

where $\rho_t^{(i)}$ is the calculated density of the total mixture at iteration (i), $\rho_{tm}^{(i)}$ is the measured density of the total mixture at iteration (i), $\mu_t^{(i)}$ is the calculated viscosity of the total mixture at iteration (i), $\mu_{tm}^{(i)}$ the measured viscosity of the total mixture at iteration (i), $\sigma_\rho^{(i)2}$ is the variance in $\rho_{tm}(i)$, $\sigma_\mu^{(i)2}$ is the variance in $\mu_{tm}(i)$, E is an error, and N is the total number of time points considered.

25. The method according to claim 24, wherein:

said least squares algorithm is an error minimization algorithm which is performed with (N) number of measured and calculated densities and viscosities of crude oil and oil filtrate in order to provide a calculation of at least one of said crude oil density and said crude oil viscosity.

26. The method according to claim 25, further comprising:

comparing determinations of said density and viscosity of the total mixture made at different sampling times to make a final estimate of the component properties.

27. The method according to claim 26, wherein:

said comparing determinations comprises comparing determinations of said density and viscosity to determine whether said comparisons are within a desired tolerance.

\* \* \* \* \*

UNITED STATES PATENT AND TRADEMARK OFFICE
CERTIFICATE OF CORRECTION

PATENT NO.           : 7,134,500 B2                                           Page 1 of 1
APPLICATION NO. : 10/741078
DATED                   : November 14, 2006
INVENTOR(S)         : Terizhandur S. Ramakrishnan and Soraya Sofia Betancourt It is certified that error appears in the above-identified patent and that said Letters Patent is hereby corrected as shown below:

On the title page, item [54] and column 1, line 1:

Title should read as follows:

FORMATION FLUID CHARACTERIZATION USING FLOWLINE VISCOSITY AND DENSITY DATA IN AN OIL-BASED MUD ENVIRONMENT

Signed and Sealed this

Eighth Day of May, 2007

JON W. DUDAS
*Director of the United States Patent and Trademark Office*